(12) United States Patent
Liu et al.

(10) Patent No.: US 6,593,108 B1
(45) Date of Patent: Jul. 15, 2003

(54) NUCLEIC ACID MOLECULE ENCODING A MELANIN-CONCENTRATING HORMONE RECEPTOR 2 POLYPEPTIDE

(75) Inventors: Qingyun Liu, North Wales, PA (US); Terrence P. McDonald, Langhorne, PA (US); Andrew D. Howard, Park Ridge, NJ (US)

(73) Assignees: Merck & Co., Inc., Rahway, NJ (US); Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/712,368

(22) Filed: Nov. 14, 2000

Related U.S. Application Data
(60) Provisional application No. 60/165,871, filed on Nov. 16, 1999, provisional application No. 60/188,977, filed on Mar. 13, 2000, and provisional application No. 60/198,029, filed on Apr. 18, 2000.

(51) Int. Cl.$^7$ .................. C07H 21/04; C07K 1/00; C07K 2/00; C12N 5/00; C12N 15/00
(52) U.S. Cl. .................. 435/69.1; 435/70.1; 435/252.3; 435/254.11; 435/320.1; 435/325; 530/300; 530/350; 536/23.1; 536/23.5
(58) Field of Search ................................ 530/300, 350; 536/23.1, 23.5; 435/4, 69.1, 70.1, 325, 252.3, 320.1, 254.11

(56) References Cited

U.S. PATENT DOCUMENTS
| | | |
|---|---|---|
| 5,686,597 A | 11/1997 | Coleman et al. |
| 6,033,872 A | 3/2000 | Bergsma et al. |

FOREIGN PATENT DOCUMENTS
| | | |
|---|---|---|
| EP | 1 033 401 A2 | 2/2000 |
| WO | WO 94/01548 * | 1/1994 |
| WO | WO 00/49046 | 8/2000 |
| WO | WO 01/07606 A1 | 2/2001 |
| WO | WO 01/07611 A2 | 2/2001 |
| WO | WO 01/36471 | 5/2001 |
| WO | WO 01/62797 | 8/2001 |
| WO | WO 01/70975 | 9/2001 |

OTHER PUBLICATIONS

Lakaye et al. Cloning of the rat brain cDNA encoding for the SLC-1 G protein-coupled receptor reveals the presence of an intron in the gene. Biochim Biophys Acta 1401: 216–220, 1998.*

Mahairas et al. Genbank Accession No. AQ190629. Nov. 04, 1998. EST database.*

Tan et al. Melanin-concentrating hormone receptor subtypes 1 and 2: species-specific gene expression. 79(6): 785–792, 2002.*

Rodriquez et al. Cloning and molecular characterization of the novel human melanin-concentrating hormone receptor MCH2. Molec Pharmacol 60: 632–639, 2001.*

Bednarek et al. Short segment of human melanin-concentrating hormone that is sufficient for full activation of human melanin-concentrating hormone receptors 1 and 2. Biochem 40: 9379–9386, 2001.*

Brenner, S.E. Errors in genome function. Trends in Genetics 15(4): 132–133, 1999.*

Bork et al. Go hunting in sequence databases but watch out for the traps. Trends in Genetics. 12(10): 425–427, 1996.*

Wells. J.A. Additivity of mutational effects in proteins. Biochemistry 29 (37): 8509–8517, 1990.*

Ngo et al. Computational complexity, protein structure prediction, and the Levinthal paradox. The Protein Folding Problem and Tertiary Structure Prediction, pp. 492–495, 1994.*

Skolnick et al. From genes to protein structure and function: novel applications of computational approaches in the genomic era. Trends in Biotech 18(1):34–39, 2000.*

Bork. A. Powers and pitfalls in sequence analysis: the 70% hurdle. Genome Res 10: 398–400, 2000.*

Doerks et al. Protein annotation: detective work for function prediction. Trends in Genetics 14(6): 248–250, 1998.*

Smith et al. The challenges of genome sequence annotation or "The devil is in the details". Nature Biotech 15: 1222–1223, 1997.*

Breton, C. et al., Isolation and characterization of the human melanin-concentrating hormone gene and a variant gene, Molecular Brain Research, vol. 18, pp. 297–310, 1993.

Qu, D. et al., A role for melanin-concentrating hormone in the central regulation of feeding behaviour, Nature, vol. 380, pp. 243–247, 1996.

Erickson, J. C. et al., Sensitivity to leptin and susceptibility to seizures of mice lacking neuropeptide Y, Nature, vol. 381, pp. 415–418, 1996.

Chambers, J. et al., Melanin-concentrating hormone is the cognate ligand for the orphan G-protein-coupled receptor SLC-1, Nature, vol. 400, pp. 261–265, 1999.

Saito, Y. et al., Molecular characterization of the melanin-concentrating-hormone receptor, Nature, vol. 400, pp. 265–269, 1999.

Bachner, D. et al., Identification of melanin concentrating hormone (MCH) as the natural ligand for the orphan somatostatin-like receptor 1 (SLC-1), FEBS Letters, vol. 457, pp. 522–524, 1999.

(List continued on next page.)

Primary Examiner—Elizabeth Kemmerer
Assistant Examiner—Bridget E. Bunner
(74) Attorney, Agent, or Firm—Sheldon O. Heber; Jack L. Tribble

(57) ABSTRACT

The present invention features HG67 nucleic acids and HG67 polypeptides. HG67, also referred to herein as "MCH-R2", is a G-protein coupled receptor having a high degree of sequence identity with MCH-R1. The amino acid sequence for HG67 is provided by SEQ. ID. NO. 1. The cDNA sequence of HG67 is provided by SEQ. ID. NO. 2.

14 Claims, 6 Drawing Sheets

OTHER PUBLICATIONS

Shimomura, Y. et al., Isolation and Identification of Melanin–Concentrating Hormone as the Endogenous Ligand of the SLC–1 Receptor, Biochemical and Biophysical Research Communications, vol. 261, pp. 622–626, 1999.

Mahairas, G. G. et al., Sequence–tagged connectors: A sequence approach to mapping and scanning the human genome, Proc. Natl. Acad. Sci. USA, vol. 96, pp. 9739–9744, 1999.

Nahon, J.–L., The Melanin–Concentrating Hormone: From the Peptide to the Gene, Criticial Reviews in Neurobiology, vol. 8(4), pp. 221–262, 1994.

Gen–Bank Accession No. H04706, Jun. 20, 1995.

Gen–Bank Accession No. AQ747249, Jul. 19, 1999.

* cited by examiner

SEQ. ID. NO. 3

GCTTGGATCGGGAACGAATTCATTCTTTGTTTCTAATATACCCTGGTTTTGT
GATTTTTTTTCTTGCACTGAATTGCAAATAAAACTGAGTCAAAAAGAATGA
TTAGAAAAAGGAGATTTTTGTGTTTTATGTTTTCCATTAAAAATATTCCTCT
GTGAAAGTTGAACAAAATATTCTTAAGTAATCAGTTCTACAGTGAAACAAAG
GAAGAAACCTCTGCTGTTATAAACCAAACTGGTGTTGGAATTGGAATGAG
CTTGGGGAAGCACAGGCACCTCTGAATTATATTAAGATATTTCAAAGTCTTT
CACTTACCTGTCCACACTCATTACAGTCATGATGGCACTACAGGCAAATTGG
TTACAAGTATCCAGGGATGTGATGATGGTGCAGAGAGGCCCCCCAAACACC
CACTCTCCCCCTCGGGCCCATTGGTGAATAAGAAAGGCATTCCAACTATGT
GGACCAAATCAGCCACAGCCAGGTTGCAGATATAGATGTCAGGGACTGTTT
TTTTCCTGGATCTGAAAGAGATAGAGGAAACTGAGGATTGACATTGAATGTG
TACAGACTATTCGATATATGCTACCTCATACACAATTTTTAATTGACATTATG
CGTTTTTAAATGGTAAGGAGAACCCTTTCCCATTGCCTTAAAGGACTTCGC
CNNCCTGGGGGTGTTTTAAAGCATTTGGACCAATTTATTTGATAACTACTGG
GGGGGTTAAAAATATGTCCACAAATATTTGATATTCCCTTCAGTAGGTGGAG
CCTAATTCCCTCTGAGTGCTGACCTTATTAACTTGCTCTAACAATGAGATTT
GGGCGAAGTGCAGGGTGTGACTTTAAATAAGTACAAATTTTTGGGGGCTTCT
CTTGTCTCTGTGGATTGCTTCCTGAGGAGCCGCTCATCTGA

FIG. 1

```
            1                                                              50
SEQ ID NO 2 ..........  ..........  ..........  ..........  ..........
SEQ ID NO 4 TCAGATGAGC  GGCTCCTCAG  GAAGCAATCC  ACAGAGACAA  GAGAAGCCCC 51                                                             100
SEQ ID NO 2 ..........  ..........  ..........  ..........  ..........
SEQ ID NO 4 CAAAAATTTG  TACTTATTTA  AAGTCACACC  CTGCACTTCG  CCCAAATCTC 101                                                            150
SEQ ID NO 2 ..........  ..........  ..........  ..........  ..........
SEQ ID NO 4 ATTGTTAGAG  CAAGTTAATA  AGGTCAGCAC  TCAGAGGGAA  TTAGGCTCCA 151                                                            200
SEQ ID NO 2 ..........  ..........  ..........  ..........  ..........
SEQ ID NO 4 CCTACTGAAG  GGAATATCAA  ATATTTGTGG  ACATATTTTT  AACCCCCCCA 201                                                            250
SEQ ID NO 2 ......ATGA  ATCCATTTCA  TGCATCT.TG  TTGGAACACC  TC.....TGC
SEQ ID NO 4 GTAGTTATCA  AATAAATTGG  TCCAAATGCT  TTAAAACACC  CCCAGGNNGG 251                                                            300
SEQ ID NO 2 CGAACTTTTA  AACAAATCCT  GGAATAAAGA  GTTTGCTTAT  CAAACTGCCA
SEQ ID NO 4 CGAAGTCCTT  TA.AGGCAAT  GGGA.AAGGG  TTCTCCTTTA  CCATTTAAAA 301                                                            350
SEQ ID NO 2 GTGTGGTAGA  TACAGTCATC  CTCCCTTCCA  TGATTGGGAT  TATCTGTTCA
SEQ ID NO 4 ACGCATAATG  TCAATTAAAA  ATTGTGTATG  AGGTAGCATA  TATCGAATAG 351                                                            400
SEQ ID NO 2 ACAGGGCTGG  TTGGCAAC..  ATCCTCATTG  TATTC.ACTA  TAATAAGATC
SEQ ID NO 4 TCTGTACACA  TTCAATGTCA  ATCCTCAGTT  TCCTCTATCT  CTTTCAGATC 401                                                            450
SEQ ID NO 2 CAGGAAAAAA  ACAGTCCCTG  ACATCTATAT  CTGCAACCTG  GCTGTGGCTG
SEQ ID NO 4 CAGGAAAAAA  ACAGTCCCTG  ACATCTATAT  CTGCAACCTG  GCTGTGGCTG 451                                                            500
SEQ ID NO 2 ATTTGGTCCA  CATAGTTGGA  ATGCCTTTTC  TTATTCACCA  ATGGGCCCGA
SEQ ID NO 4 ATTTGGTCCA  CATAGTTGGA  ATGCCTTTTC  TTATTCACCA  ATGGGCCCGA 501                                                            550
SEQ ID NO 2 GGGGGAGAGT  GGGTGTTTGG  GGGGCCTCTC  TGCACCATCA  TCACATCCCT
SEQ ID NO 4 GGGGGAGAGT  GGGTGTTTGG  GGGGCCTCTC  TGCACCATCA  TCACATCCCT 551                                                            600
SEQ ID NO 2 GGATACTTGT  AACCAATTTG  CCTGTAGTGC  CATCATGACT  GTAATGAGTG
SEQ ID NO 4 GGATACTTGT  AACCAATTTG  CCTGTAGTGC  CATCATGACT  GTAATGAGTG 601                                                            650
SEQ ID NO 2 TGGACAGGTA  CTTTGCCCTC  GTCCAACCAT  TTCGACTGAC  ACGTTGGAGA
SEQ ID NO 4 TGGACAGGTA  AGTGAAAGAC  TTTGAAATAT  CTTAAT..AT  AATTCAGAGG
```

FIG. 2A

```
              651                                                              700
SEQ ID NO 2   ACAAGGTACA AGACCATCCG GATCAATTTG GGCCTTTGGG CAGCTTCC.T
SEQ ID NO 4   TGCCTGTGC. ..TTCCCCAA GCTCATTCCA ATTCCAACAC CAGTTTTGGT 701                                                              750
SEQ ID NO 2   TTATCCTGGC ATTGCCTGTC TGGGTCTACT CGAAGGTCAT CAAATTTAAA
SEQ ID NO 4   TTATAACAGC AGAGGTTTTC TTCCTTTGTT TCACTGT... .AGAACTGAT 751                                                              800
SEQ ID NO 2   GACGGTGTTG AGAGTTGTGC TTTTGATTTG ACATCCCTG ACGATGTACT
SEQ ID NO 4   TAC....TTA AGAATA.... .TTTTGTTCA ACTTTCACAG AGGA.ATATT 801                                                              850
SEQ ID NO 2   CTGGTATACA CTTTATTTGA CGATAACAAC TTTTTTTTTC CCTCTACCCT
SEQ ID NO 4   TTTA.ATGGA AAACATAAAA CACAAAAATC TCCTTTTTTC TAATCATTCT 851                                                              900
SEQ ID NO 2   TGATTTGGT GTGCTATATT TTAATTTTAT GCTATACTTG GGAGATGTAT
SEQ ID NO 4   T..TTTGACT CAGTTTTATT TGCAATTCA. ...GTGCAAG AAAAAAAAAT 901                                                              950
SEQ ID NO 2   CAACAGAATA AGG.ATGCCA GATGCTGCAA TCCCAGT.GT ACCAAAACAG
SEQ ID NO 4   CACAAAACCA GGGTATATTA GAAACAAAGA ATGAATTCGT TCCCGATCCA 951                                                              1000
SEQ ID NO 2   AGAGTGATGA AGTTGACAAA GATGGTGCTG GTGCTGGTGG TAGTCTTTAT
SEQ ID NO 4   AGC....... .......... .......... .......... ..........

1001                                                             1050
SEQ ID NO 2   CCTGAGTGCT GCCCCTTATC ATGTGATACA ACTGGTGAAC TTACAGATGG
SEQ ID NO 4   .......... .......... .......... .......... ..........

1051                                                             1100
SEQ ID NO 2   AACAGCCCAC ACTGGCCTTC TATGTGGGTT ATTACCTCTC CATCTGTCTC
SEQ ID NO 4   .......... .......... .......... .......... ..........

1101                                                             1150
SEQ ID NO 2   AGCTATGCCA GCAGCAGCAT TAACCCTTTT CTCTACATCC TGCTGAGTGG
SEQ ID NO 4   .......... .......... .......... .......... ..........

1151                                                             1200
SEQ ID NO 2   AAATTCCAG AAACGTCTGC CTCAAATCCA AGAAGAGCG ACTGAGAAGG
SEQ ID NO 4   .......... .......... .......... .......... ..........

1201                                         1241
SEQ ID NO 2   AAATCAACAA TATGGGAAAC ACTCTGAAAT CACACTTTTA G
SEQ ID NO 4   .......... .......... .......... .......... .
```

FIG.2B

NUCLEIC ACID MOLECULE ENCODING A MELANIN-CONCENTRATING HORMONE RECEPTOR 2 POLYPEPTIDE

CROSS-REFERENCE TO RELATED APPLICATIONS

The present application claims priority to provisional applications U.S. Ser. No. 60/165,871, filed Nov. 16, 1999, U.S. Ser. No. 60/188,977, filed Mar. 13, 2000, and U.S. Ser. No. 60/198,029, filed Apr. 18, 2000, each of which are hereby incorporated by reference herein.

BACKGROUND OF THE INVENTION

The references cited herein are not admitted to be prior art to the claimed invention.

Neuropeptides present in the hypothalamus play a major role in mediating the control of body weight. (Flier, et al., 1998. *Cell*, 92, 437–440.) Melanin-concentrating hormone (MCH) is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol.* 4, 632–637.) MCH was first identified in salmon pituitary, and in fish MCH affects melanin aggregation thus affecting skin pigmentation. In trout and in eels MCH has also been shown to be involved in stress induced or CRF-stimulated ACTH release. (Kawauchi, et al., 1983. *Nature* 305, 321–323.)

In humans two genes encoding MCH have been identified that are expressed in the brain. (Breton, et al., 1993. *Mol. Brain Res.* 18, 297–310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063–1073.)

Pharmacological and genetic evidence suggest that the primary mode of MCH action is to promote feeding (orexigenic). MCH mRNA is up regulated in fasted mice and rats, in the ob/ob mouse and in mice with targeted disruption in the gene for neuropeptide Y (NPY). (Qu, et al., 1996. *Nature* 380, 243–247, and Erickson, et al., 1996. *Nature* 381, 415–418.) Injection of MCH centrally (ICV) stimulates food intake and MCH antagonizes the hypophagic effects seen with α melanocyte stimulating hormone (αMSH). (Qu, et al., 1996. *Nature* 380, 243–247.) MCH deficient mice are lean, hypophagic and have increased metabolic rate. (Shimada, et al., 1998. *Nature* 396, 670–673.)

MCH action is not limited to modulation of food intake as effects on the hypothalamic-pituitary-axis have been reported. (Nahon, 1994. *Critical Rev. in Neurobiol.* 8, 221–262.) MCH may be involved in the body response to stress as MCH can modulate the stress-induced release of CRF from the hypothalamus and ACTH from the pituitary. In addition, MCH neuronal systems may be involved in reproductive or maternal function.

Several references describe a receptor that is indicated to bind MCH ("MCH-R1"). (Chambers, et al., 1999. *Nature* 400, 261–265; Saito, et al., 1999. *Nature* 400, 265–269; B̈achner, et al., 1999. *FEBS Letters* 457:522–524; and Shimomura, et al., 1999. *Biochemical and Biophysical Research Communications* 261, 622–626.)

SUMMARY OF THE INVENTION

The present invention features HG67 nucleic acids and HG67 polypeptides. HG67, also referred to herein as "MCH-R2", is a G-protein coupled receptor having a high degree of sequence identity with MCH-R1. The amino acid sequence for HG67 is provided by SEQ. ID. NO. 1. The cDNA sequence of HG67 is provided by SEQ. ID. NO. 2.

HG67 polypeptides contain a region of at least 9 contiguous amino acids that is present in SEQ. ID. NO. 1. Such polypeptides may contain additional regions present, or not present, in SEQ. ID. NO. 1. HG67 polypeptides include, for example, full length HG67, HG67 fragments, and chimeric polypeptides containing all or a portion of HG67 along with amino acid region(s) not from HG67.

HG67 nucleic acids contain a region that encodes for a HG67 polypeptide or contains at least 18 contiguous nucleotides that is present in SEQ. ID. NO. 2 or the complement thereof. Such nucleic acid may contain additional regions present, or not present, in nucleic acid encoding for HG67 or present in SEQ. ID. NO. 2 or the complement thereof. HG67 nucleic acids include, for example, nucleic acid encoding for all or a portion of HG67, nucleic acid containing all or a portion of SEQ. ID. NO. 2, and recombinant nucleic acid encoding all or a portion of HG67 and/or containing all or a portion of SEQ. ID. NO. 2.

Thus, a first aspect of the present invention describes a purified HG67 polypeptide. The polypeptide comprises at least 9 contiguous amino acids of SEQ. ID. NO. 1.

A "purified polypeptide" represents at least 10% of the total protein present in a sample or preparation. In preferred embodiments, the purified polypeptide represents at least about 50%, at least about 75%, or at least about 95% of the total protein in a sample or preparation. Reference to "purified polypeptide" does not require that the polypeptide has undergone any purification and may include, for example, chemically synthesized polypeptide that has not been purified.

Another aspect of the present invention describes a purified HG67 nucleic acid. The nucleic acid comprises either (a) a region of at least 18 contiguous bases present in either bases 1–180 or 396–1020 of SEQ. ID. NO. 2, or the complement thereof; or (b) a region encoding for at least 9 contiguous amino acids present in either bases 1–60 or 150–340 of SEQ. ID. NO. 1. Reference to the presence of one region does not indicate that another region is not present. For example, in different embodiments the nucleic acid can comprise or consist of a nucleic acid encoding for SEQ. ID. NO. 1 and can comprise or consist of the nucleic acid sequence of SEQ. ID. NO. 2.

A "purified nucleic acid" represents at least 10% of the total nucleic acid present in a sample or preparation. In preferred embodiments, the purified nucleic acid represents at least about 50%, at least about 75%, or at least about 95% of the total nucleic acid in a sample or preparation. Reference to "purified nucleic acid" does not require that the nucleic acid has undergone any purification and may include, for example, chemically synthesized nucleic acid that has not been purified.

Another aspect of the present invention describes an expression vector. The expression vector comprises a nucleotide sequence encoding for at least 9 contiguous amino acids provided in SEQ. ID. NO. 1, wherein the nucleotide sequence is transcriptionally coupled to an exogenous promoter. Reference to a nucleotide sequence "transcriptionally coupled to an exogenous promoter" indicates the presence and positioning of an RNA promoter such that it can mediate transcription of the nucleotide sequence and that the promoter is not naturally associated with the nucleotide sequence.

Another aspect of the present invention describes a recombinant cell comprising an expression vector encoding for a region of at least 9 contiguous amino acids of SEQ. ID. NO. 1. The expression vector contains a promoter that is transcriptionally coupled to nucleic acid encoding for the region and is recognized by an RNA polymerase present in the cell.

Another aspect of the present invention describes a recombinant cell made by a process comprising the step of introducing into the cell an expression vector encoding for a region of at least 9 contiguous amino acids of SEQ. ID. NO. 1. Preferably, the expression vector contains a promoter that is transcriptionally coupled to nucleic acid encoding for the region and is recognized by an RNA polymerase present in the cell. The expression vector can be used to insert recombinant nucleic acid into the host genome or can exist as an autonomous piece of nucleic acid.

Another aspect of the present invention features a purified antibody preparation comprising an antibody that binds to HG67. A "purified antibody preparation" is a preparation where at least 10% of the antibodies present bind to HG67. In preferred embodiments, antibodies binding to HG67 represent at least about 50%, at least about 75%, or at least about 95% of the total antibodies present. Reference to "purified antibody preparation" does not require that the antibodies in the preparation have undergone any purification.

Another aspect of the present invention describes a method of producing a polypeptide comprising at least 9 contiguous amino acids of SEQ. ID. NO. 1. The method involves the step of growing a recombinant cell able to express the polypeptide from an expression vector.

Another aspect of the present invention describes a method for screening for a compound able to bind to HG67. The method involves the following steps: (a) expressing a polypeptide comprising at least about 9 contiguous amino acids of SEQ. ID. NO. 1 from recombinant nucleic acid; (b) providing to the polypeptide a test preparation comprising one or more test compounds; and (c) measuring the ability of the test preparation to bind to the polypeptide.

A test preparation contains one or more compounds being tested. In different embodiments a test preparation contains 10 or more compounds, 5 or more compounds, or 1 compound.

A "recombinant nucleic acid" is a nucleic acid containing one or more regions not naturally associated with each other. Examples of recombinant nucleic acid include an HG67 region present on a nucleic acid also containing one or more regulatory elements not naturally associated with the HG67 region, viral elements, or selectable markers.

Another aspect of the present invention describes a method for screening for HG67 activity. The method involves (a) contacting a cell expressing a recombinant nucleic acid encoding for a G-protein coupled receptor comprising at least 9 contiguous bases of SEQ. ID. NO. 1 with a test preparation comprising one or more test compounds; and (b) measuring the effect of the test preparation on the activity of the receptor.

Another aspect of the present invention describes a method for achieving a beneficial effect in a patient comprising the step of modulating HG67 activity in the patient. Preferably, HG67 activity is modulated by causing a decrease in the activity or expression of the receptor. HG67 activity can be modulated using, for example, organic compounds active at the HG67 receptor and nucleic acid able to decrease HG67 expression.

Another aspect of the present invention describes a method for screening for a compound able to bind HG67 or a fragment thereof. The method comprising the steps of: (a) expressing a polypeptide comprising the amino acid sequence of SEQ. ID. NO. 1 or fragment thereof from recombinant nucleic acid; (b) providing to the polypeptide a labeled MCH ligand and a test preparation comprising one or more test compounds; and (c) measuring the effect of the test preparation on binding of the labeled MCH ligand to the polypeptide.

A "MCH ligand" refers to a polypeptide that binds to HG67 at the MCH binding site. MCH ligands include human MCH, salmon MCH, and derivatives thereof.

Another aspect of the present invention describes a method for screening for a compound able to modulate HG67 activity. The method comprises the steps of: (a) contacting a cell line expressing recombinant nucleic acid encoding for a polypeptide comprising (i) the amino acid sequence of SEQ. ID. NO. 1 or a fragment thereof that binds MCH and (ii) a region that functionally couples to a G protein, wherein the polypeptide is able to transduce an intracellular signal upon MCH ligand binding, with a MCH ligand and a test preparation comprising one or more test compounds; and (b) measuring the effect of the preparation on polypeptide activity.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE FIGURES

FIG. 1 illustrates the nucleic acid sequence of GenBank Accession Number AQ747249 (SEQ. ID. NO. 3).

FIGS. 2A and 2B illustrate a comparison of SEQ. ID. NO. 2 with SEQ. ID. NO. 4. SEQ. ID. NO. 4 is the anti-strand of SEQ. ID. NO. 3.

DETAILED DESCRIPTION OF THE INVENTION

Figure 3:
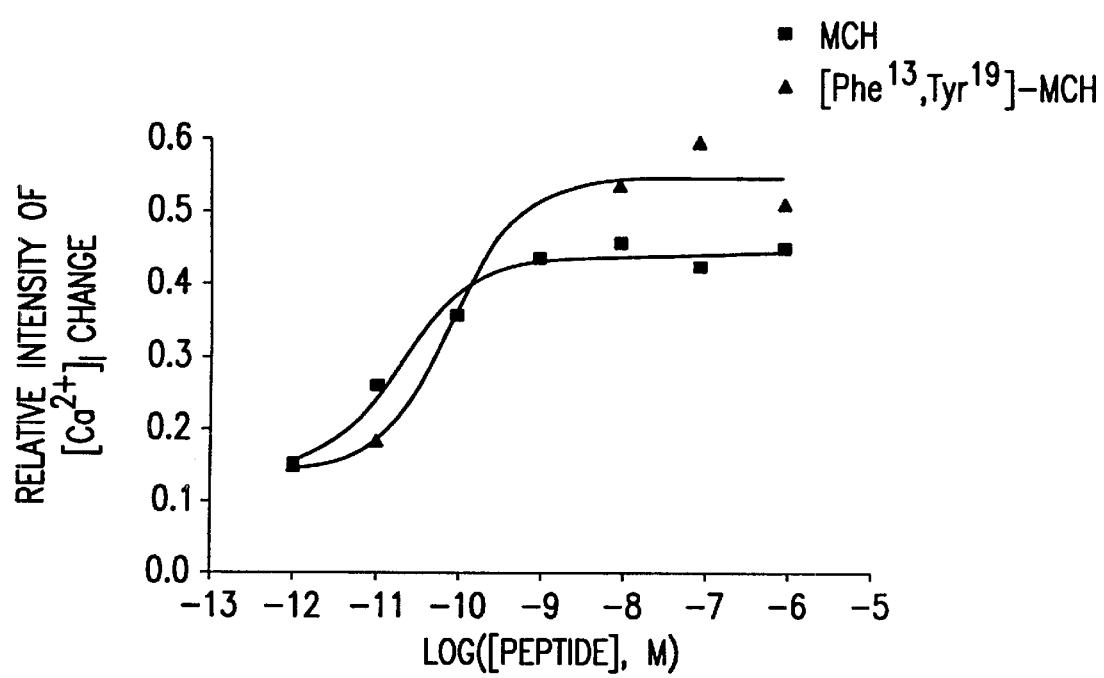
FIG. 3 illustrates $[Ca^{2+}]_i$ by MCH and $[Phe^{13}, Tyr^{19}]$-MCH in the HEK293T cells transiently expressing HG67.

HG67 is a G-protein coupled receptor having an amino acid sequence identity of 39% with MCH-R1. An internal region of HG67 is similar to an internal region of a deposited genomic nucleic acid sequence described in GenBank Accession Number AQ747249 (FIG. 1, SEQ. ID. NO. 3). FIG. 2, provides a comparison between SEQ. ID. NO. 2 and SEQ. ID. NO. 4 (the anti-sense strand of SEQ. ID. NO. 3).

The utilities exemplified and enabled herein include utilities not dependent upon HG67 being an MCH receptor. For example, HG67 nucleic acid was cloned from a human source (see Example 1). Such nucleic acid can be used as hybridization probes to distinguish between cells that produce HG67 transcripts from human or non-human cells (including bacteria) that do not produce such transcripts.

Similarly, antibodies specific for HG67 can be used to distinguish between cells that express HG67 from human or non-human cells (including bacteria) that do not express HG67.

Based on HG67 being a MCH receptor, HG67 provides a target to achieve a beneficial effect in a patient. Preferably, HG67 activity is modulated to achieve one or more of the following: weight loss, weight gain, treat cancer (e.g., colon or breast), reduce pain, treat diabetes, reduce stress or treat sexual dysfunction.

Modulation of HG67 activity is preferably achieved by evoking a response at the MCH receptor or by altering a response evoked by a MCH receptor agonist or antagonist. Compounds modulating MCH-R receptor activity include agonists, antagonists, and allosteric modulators. Generally, HG67 antagonists and allosteric modulators negatively affecting activity will be used to achieve weight loss, treat cancer (e.g., colon or breast), reduce pain, reduce stress or teat sexual dysfunction; and HG67 agonists and allosteric modulators positively affecting activity will be used to produce a weight gain.

HG67 activity can also be affected by modulating HG67 expression. Compounds modulating HG67 expression include cloned HG67 that can express HG67 in vivo, antisense nucleic acids targeted to HG67 transcripts and enzymatic nucleic acids targeted to HG67 transcripts.

A patient refers to a mammal, preferably a human. Reference to patient does not necessarily indicate the presence of a disease or disorder. The term patient includes subjects treated prophylactically and subjects afflicted with a disease or disorder.

Preferably, HG67 activity is modulated to achieve a weight loss or to treat diabetes in a patient. Diabetes mellitus can be treated by modulating HG67 activity to achieve, for example, one or both of the following: enhancing glucose tolerance or decreasing insulin resistance.

Excessive weight is a contributing factor to different diseases including hypertension, diabetes, dyslipidemias, cardiovascular disease, gall stones, osteoarthritis and certain forms of cancers. Bringing about a weight loss can be used, for example, to reduce the likelihood of such diseases and as part of a treatment for such diseases. Weight reduction can be achieved by modulating HG67 activity to obtain, for example, one or more of the following effects: reducing appetite, increasing metabolic rate, reducing fat intake or reducing carbohydrate craving.

In another embodiment HG67 activity is modulated to increase weight in a patient. Increasing weight is particularly useful for a patient having a disease or disorder, or under going a treatment, accompanied by weight loss. Examples of diseases or disorders accompanied by weight loss include anorexia, AIDS, wasting, cachexia, and frail elderly. Examples of treatments accompanied by weight loss include chemotherapy and radiation therapy.

HG67 Polypeptides

HG67 polypeptides contain a HG67 region that is at least 9 contiguous amino acids in length. HG67 polypeptides have a variety of uses, such as providing a component for a functional receptor; being used as an immunogen to produce antibodies binding to HG67; being used as a target to identify compounds binding to the HG67; and/or being used in assays to measure the ability of a compound to effect HG67 activity.

In chimeric polypeptides containing one or more regions from HG67 and one or more regions not from HG67, the region(s) not from HG67 can be used, for example, to achieve a particular purpose or to produce a polypeptide that can substitute for HG67 or a fragment thereof. Particular purposes that can be achieved using chimeric HG67 polypeptides include providing a marker for isolation, functional analysis of different receptor regions, enhancing an immune response, and altering G-protein coupling.

Preferably, a HG67 polypeptide comprises or consists of the amino acid sequence of SEQ. ID. NO. 1. In additional embodiments a HG67 polypeptide comprises or consists of a SEQ. ID. NO. 1 contiguous region at least 18 amino acids in length, at least 27 amino acids in length, at least 54 amino acids in length or a region that is selected from the group consisting of: amino acids 1–10, 11–20, 21–30, 31–40, 41–50, 51–60, 61–70, 71–80, 81–90, 91–100, 101–110, 111–120, 121–130, 131–140, 141–150, 151–160, 161–170, 171–180, 181–190, 191–200, 201–210, 211–220, 221–230, 231–240, 241–250, 251–260, 261–270, 271–280, 281–290, 291–300, 301–310, 311–320, 321–330, and 331–340 of SEQ. ID. NO. 1. In another embodiment the HG67 polypeptide comprises or consists of a sequence selected from the group consisting of:

MNPFHASCWNTSA (SEQ. ID. NO. 5);
MIGIICSTGLV (SEQ. ID. NO. 6);
MYQQNKDARCCNPS (SEQ. ID. NO. 7);
MVLVLVVVFILSAA (SEQ. ID. NO. 8); and
MEQPTLAFYVGYYLSI (SEQ. ID. NO. 9).

HG67 polypeptides also include functional G-protein receptors that respond to MCH and have a sequence similarity of at least about 85%, preferably at least 95% with SEQ. ID. NO. 1. Sequence similarity for polypeptides can be determined by BLAST. (Altschul, et al., 1997. *Nucleic Acids Res.* 25, 3389–3402, hereby incorporated by reference herein.) In one embodiment sequence similarity is determined using tBLASTn search program with the following parameters: MATRIX:BLOSUM62, PER RESIDUE GAP COST: 11, and Lambda ratio: 1.

Polypeptides can be produced using standard techniques including those involving chemical synthesis and those involving biochemical synthesis. Techniques for chemical synthesis of polypeptides are well known in the art. (See e.g., Vincent, in *Peptide and Protein Drug Delivery*, New York, N.Y., Dekker, 1990.)

Biochemical synthesis techniques for polypeptides are also well known in the art. Such techniques employ a nucleic acid template for polypeptide synthesis. The genetic code providing the sequences of nucleic acid triplets coding for particular amino acids is well known in the art. (See, e.g., Lewin *GENES IV*, p. 119, Oxford University Press, 1990.) Examples of techniques for introducing nucleic acid into a cell and expressing the nucleic acid to produce protein are provided in references such as Ausubel, *Current Protocols in Molecular Biology*, John Wiley, 1987–1998, and Sambrook, et al., in *Molecular Cloning, A Laboratory Manual*, 2$^{nd}$ Edition, Cold Spring Harbor Laboratory Press, 1989.

Functional HG67

Functional HG67 transduces a G-protein coupled intracellular signal upon ligand binding. The identification of the amino acid and nucleic acid sequences of HG67 provide tools for obtaining functional receptors related to HG67 from other sources, for producing HG67 chimeric G-protein coupled receptors, and for producing functional derivatives of SEQ. ID. NO. 1.

HG67 polypeptides can be readily identified and obtained based on their sequence similarity to HG67. Both the amino acid and nucleic acid sequences of HG67 can be used to help identify and obtain HG67 polypeptides. For example, SEQ.

ID. NO. 1 can be used to produce degenerative nucleic acid probes or primers for identifying and cloning nucleic acid encoding for a HG67 polypeptide, and SEQ. ID. NO. 2 or fragments thereof, can be used under conditions of moderate stringency to identify and clone nucleic acid encoding HG67 polypeptides.

The use of degenerative probes and moderate stringency conditions for cloning is well known in the art. Examples of such techniques are described by Ausubel, *Current Protocols in Molecular Biology*, John Wiley, 1987–1998, and Sambrook, et al., in *Molecular Cloning, A Laboratory Manual*, 2$^{nd}$ Edition, Cold Spring Harbor Laboratory Press, 1989.

Starting with HG67 obtained from a particular source, derivatives can be produced having receptor activity. Such derivatives include polypeptides with amino acid substitutions, additions and deletions. Changes to HG67 to produce a derivative having essentially the same properties should be made outside of the HG67 binding domain and in a manner not altering the tertiary structure. The ability of a polypeptide to have HG67 activity can be confirmed using techniques such as those measuring G-protein activity.

Differences in naturally occurring amino acids are due to different R groups. An R group effects different properties of the amino acid such as physical size, charge, and hydrophobicity. Amino acids are can be divided into different groups as follows: neutral and hydrophobic (alanine, valine, leucine, isoleucine, proline, tyrptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

Changes outside of different amino acid groups can also be made. Preferably, such changes are made taking into account the position of the amino acid to be substituted in the polypeptide. For example, arginine can substitute more freely for nonpolor amino acids in the interior of a polypeptide then glutamate because of its long aliphatic side chain. (See, Ausubel, *Current Protocols in Molecular Biology*, John Wiley, 1987–1998, Supplement 33 Appendix 1C.)

HG67 Antibodies

Antibodies recognizing HG67 can be produced using a polypeptide containing SEQ. ID. NO. 1 or a fragment thereof as an immunogen. Preferably, a polypeptide used as an immunogen consists of a polypeptide of SEQ. ID. NO. 1 or a SEQ. ID. NO. 1 fragment at least 9 amino acids in length.

Antibodies to HG67 have different uses such as being used to identify the presence of HG67 and to isolate HG67 polypeptides. Identifying the presence of HG67 can be used, for example, to identify cells producing HG67. Such identification provides an additional source of HG67 and can be used to distinguish cells known to produce HG67 from cells that do not produce HG67. For example, antibodies to HG67 can distinguish human cells expressing HG67 from human cells not expressing HG67 or non-human cells (including bacteria) that do not express HG67.

Techniques for producing and using antibodies are well known in the art. Examples of such techniques are described in Ausubel, *Current Protocols in Molecular Biology*, John Wiley, 1987–1998, Harlow, et al., *Antibodies, A Laboratory Manual*, Cold Spring Harbor Laboratory, 1988, and Kohler, et al., *Nature* 256:495–497, 1975.

Binding Assay

HG67 or a fragment thereof can be used in binding studies to identify compounds binding to the receptor. Such studies can be performed using different formats including competitive and non-competitive formats. Further competition studies can be carried out using additional compounds determined to bind to HG67.

The particular HG67 sequence involved in ligand binding can be readily identified by using labeled compounds that bind to the receptor and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding to a compound can be subdivided to further locate the binding region. Fragments used for binding studies can be generated using recombinant nucleic acid techniques.

Preferably, binding studies are performed using HG67 expressed from a recombinant nucleic acid. More preferably, recombinantly expressed HG67 consists of the SEQ. ID. NO. 1 amino acid sequence.

Binding assays can be performed using individual compounds or preparations containing different numbers of compounds. A preparation containing different numbers of compounds having the ability to bind to HG67 can be divided into smaller groups of compounds that can be tested to identify the compound(s) binding to HG67.

Binding assays can be performed using recombinantly produced HG67 present in different environments. Such environments include, for example, cell extracts and purified cell extracts containing the HG67 recombinant nucleic acid; and also include, for example, the use of a purified HG67 receptor polypeptide produced by recombinant means which is introduced into a different environment.

The identification of MCH as a ligand for HG67 provides a means for producing receptor activity, and provides a target for binding to the receptor and for altering receptor activity. MCH ligands can readily be designed based on the structure of MCH. Examples of MCH ligands include human MCH, salmon MCH, and derivatives thereof. Suitable derivatives can be identified empirically, for example, by deleting or substituting one or more amino acids of human MCH and testing the resulting polypeptide. Techniques for producing a polypeptide of a particular sequence are well known in the art. ($Phe^{13}Tyr^{19}$)-MCH is an example of an MCH derivative that binds HG67.

Different types of labels for MCH ligands can be employed. Examples of such labels include radiolabels, luminescent molecules, haptens and enzyme substrates. The ability of a particular label to interfere with binding can readily be determined by comparing the ability of MCH labeled with the particular label to compete against MCH binding.

Functional Assays

Assays involving a functional G-protein receptor containing one or more HG67 regions can be employed for different purposes such as selecting for compounds active at HG67, evaluating the ability of a compound to effect receptor activity, and mapping the activity of different HG67 regions. HG67 activity can be measured using different techniques such as detecting a change in the intracellular conformation of HG67, measuring G-protein activity, or measuring the level of intracellular messengers.

Recombinantly expressed receptor can be used to facilitate determining whether a compound is active at that receptor or another receptor. For example, HG67 can be expressed by an expression vector in a cell line such as HEK 293, COS 7, or CHO, not normally expressing the receptor, wherein the same cell line without the expression vector or with an expression vector not encoding HG67 can act as a control.

Techniques for measuring different G-protein activities, such as Gi, Gs, and Gq are well known in the art. Gi and Gs activity can be measured using techniques such as a melonaphore assay, assays measuring cAMP production, assays measuring inhibition of cAMP accumulation, and assays measuring binding of $^{35}$S-GTP. cAMP can be measured using different techniques such as radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button, et al., 1993. *Cell Calcium* 14, 663–671, and Feighner, et al., 1999. *Science* 284, 2184–2188, both of which are hereby incorporated by reference herein.)

Chimeric HG67 can be used to assay for compounds active at the receptor and to obtain information concerning different regions of the receptor. A chimeric HG67 receptor contains an N-terminal extracellular domain; a transmembrane domain made up of transmembrane regions (preferably 7 transmembrane regions), extracellular loop regions, and intracellular loop regions; and an intracellular carboxy terminus domain; where one or more domains comprise at least one region of at least 9 contiguous amino acids present in SEQ. ID. NO. 1. In different embodiments a chimeric HG67 contains the extracellular domain of HG67; and/or contains one or more regions of at least 18 contiguous amino acids present in SEQ. ID. NO. 1.

The specificity of G-protein coupling is determined by intracellular domain(s). Chimeric HG67 can be produced to functionally couple to a desired G-protein. Techniques for producing chimeric receptors and measuring G-protein coupled responses are provided in, for example, International Application Number WO 97/05252, U.S. Pat. No. 5,981,195, and U.S. Pat. No. 5,264,565.

Functional assays can be performed using individual compounds or preparations containing different compounds. A preparation containing different compounds where one or more compounds affect HG67 activity can be divided into smaller groups of compounds to identify the compound(s) affecting HG67 activity.

Functional assays can be performed using recombinantly produced HG67 present in different environments. Such environments include, for example, cell extracts and purified cell extracts containing the HG67 expressed from recombinant nucleic acid and an appropriate membrane for the polypeptide; and the use of a purified HG67 produced by recombinant means that is introduced into a different environment suitable for measuring G-protein activity.

Screening for HG67 receptor active compounds is facilitated through the use of a MCH ligand in the assay. The use of a MCH ligand in a screening assay provides for HG67. The effect of test compounds on such activity can be measured to identify, for example, allosteric modulators and antagonists. Additionally, such assays can be used to identify agonists.

HG67 Nucleic Acid

HG67 nucleic acid contains a region that encodes for at least 9 contiguous amino acids of SEQ. ID. NO. 1 or contains at least 18 contiguous bases present in SEQ. ID. NO.2. HG67 nucleic acid have a variety of uses, such as being used as a hybridization probe or PCR primer to identify the presence of HG67 nucleic acid; being used as a hybridization probe or PCR primer to identify nucleic acid encoding for receptors related to HG67; and/or being used for recombinant expression of HG67 polypeptides.

Regions in HG67 nucleic acid that do not encode for a HG67 segment or are not found in SEQ. ID. NO.2, if present, are preferably chosen to achieve a particular purposes. Examples of additional regions that can be used to achieve a particular purpose include capture regions that can be used as part of a sandwich assay, reporter regions that can be probed to indicate the presence of the nucleic acid, expression vector regions, and regions encoding for other polypeptides.

In different embodiments, HG67 nucleic acid comprises or consists of nucleic acid encoding for the polypeptide of SEQ. ID. NO.1, or comprises or consists of the nucleic acid sequence of SEQ. ID. NO. 2. In additional embodiments a HG67 nucleic acid comprises or consists of a sequence that encodes at least 9 contiguous amino acids, at least 18 contiguous amino acids, at least 27 contiguous amino acids, or at least 54 contiguous amino acids present in either bases 1–60 or 150–340 of SEQ. ID. NO. 1; comprises or consists of a sequence at least 18 contiguous nucleotides, at least 36 contiguous nucleotides, or at least 72 contiguous nucleotides present in bases 1–180 or 396–1020 of SEQ. ID. NO. 2, or the complement thereof; or comprises or consists of a nucleic acid sequence selected from the group consisting of:

ATGAATCCATTTCATGCATCTTGTTGG (SEQ. ID. NO. 10);

ATGATTGGGATTATCTGTTCAACA (SEQ. ID. NO. 11);

ATGTATCAACAGAATAAGGATGCCAGAT (SEQ. ID. NO.12);

ATGAAGTTGACAAAGATGGTGCTGGTG (SEQ. ID. NO.13); and

ATGGGAAACACTCTGAAATCACACTTT (SEQ. ID. NO. 14).

HG67 nucleic acid also includes nucleic acid encoding a functional G-protein that responds to MCH and has a sequence similarity of at least about 85%, preferably at least 95% with SEQ. ID. NO. 1; and nucleic acid having a sequence similarity of at least about 85%, preferably 90% with SEQ. ID. NO. 2. Sequence similarity for nucleic acid can be determined by FASTA. (Pearson 1990. *Methods in Enzymology* 183, 63–98, hereby incorporated by reference herein.) In one embodiment, sequence similarity is determined using FASTA search program with the following parameters: MATRIX: BLOSUM50, GAP PENALTIES: open=−12; residue=−2.

The guidance provided in the present application can be used to obtain the nucleic acid sequence encoding for HG67 related receptors from different sources and to construct a receptor having HG67 activity. Obtaining nucleic acids encoding for HG67 related receptors from different sources is facilitated using sets of degenerative probes and primers and by the proper selection of hybridization conditions. Sets of degenerative probes and primers are produced taking into account the degeneracy of the genetic code. Adjusting hybridization conditions is useful for controlling probe or primer specificity to allow for hybridization to nucleic acids having similar sequences.

Techniques employed for hybridization detection and PCR cloning are well known in the art. Nucleic acid detection techniques are described, for example, in Sambrook, et al., in *Molecular Cloning, A Laboratory Manual*, 2$^{nd}$ Edition, Cold Spring Harbor Laboratory Press, 1989. PCR cloning techniques are described, for example, in White, *Methods in Molecular Cloning*, volume 67, Humana Press, 1997.

HG67 probes and primers can be used to screen nucleic acid libraries containing, for example, genomic DNA or cDNA. Such libraries are commercially available, and can be produced using techniques such as those described in Ausubel, *Current Protocols in Molecular Biology*, John Wiley, 1987–1998.

Starting with a particular amino acid sequence and the known degeneracy of the genetic code, a large number of different encoding nucleic acid sequences can be obtained. The degeneracy of the genetic code arises because almost all amino acids are encoded for by different combinations of nucleotide triplets or "codons". The translation of a particular codon into a particular amino acid is well known in the art (see, e.g., Lewin *GENES* IV, p. 119, Oxford University Press, 1990). Amino acids are encoded for by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Nucleic acid having a desired sequence can be synthesized using chemical and biochemical techniques. Examples of chemical techniques are described in Ausubel, *Current Protocols in Molecular Biology*, John Wiley, 1987–1998, and Sambrook et al., in *Molecular Cloning, A Laboratory Manual*, 2$^{nd}$ Edition, Cold Spring Harbor Laboratory Press, 1989.

Biochemical synthesis techniques involve the use of a nucleic acid template and appropriate enzymes such as DNA and/or RNA polymerases. Examples of such techniques include in vitro amplification techniques such as PCR and transcription based amplification, and in vivo nucleic acid replication. Examples of suitable techniques are provided by Ausubel, *Current Protocols in Molecular Biology*, John Wiley, 1987–1998, Sambrook et al., in *Molecular Cloning, A Laboratory Manual*, 2$^{nd}$ Edition, Cold Spring Harbor Laboratory Press, 1989, and Kacian et al., U.S. Pat. No. 5,480,784.

HG67 Probes

Probes for HG67 contain a region that can specifically hybridize to HG67 target nucleic acid under appropriate hybridization conditions and can distinguish HG67 nucleic acid from non-target nucleic acids. Probes for HG67 can also contain nucleic acid that are not complementary to HG67 nucleic acid.

Preferably, non-complementary nucleic acid that is present has a particular purpose such as being a reporter sequence or being a capture sequence. However, additional nucleic acid need not have a particular purpose as long as the additional nucleic acid does not prevent the HG67 nucleic acid from distinguishing between target and non-target.

Hybridization occurs through complementary nucleotide bases. Hybridization conditions determine whether two molecules, or regions, have sufficiently strong interactions with each other to form a stable hybrid.

The degree of interaction between two molecules that hybridize together is reflected by the Tm of the produced hybrid. The higher the Tm the stronger the interactions and the more stable the hybrid. Tm is effected by different factors well known in the art such as the degree of complementarity, the type of complementary bases present (e.g., A-T hybridization versus G-C hybridization), the presence of modified nucleic acid, and solution components. (E.g., Sambrook, et al., in *Molecular Cloning, A Laboratory Manual*, 2$^{nd}$ Edition, Cold Spring Harbor Laboratory Press, 1989.)

Stable hybrids are formed when the Tm of a hybrid is greater than the temperature employed under a particular set of hybridization assay conditions. The degree of specificity of a probe can be varied by adjusting the hybridization stringency conditions. Detecting probe hybridization is facilitated through the use of a detectable label. Examples of detectable labels include luminescent, enzymatic, and radioactive labels.

Examples of stringency conditions are provided in Sambrook, et al., in *Molecular Cloning, A Laboratory Manual*, 2$^{nd}$ Edition, Cold Spring Harbor Laboratory Press, 1989. An example of high stringency conditions is as follows: Prehybridization of filters containing DNA is carried out for 2 hours to overnight at 65° C. in buffer composed of 6×SSC, 5×Denhardt's solution, and 100 μg/ml denatured salmon sperm DNA. Filters are hybridized for 12 to 48 hours at 65° C. in prehybridization mixture containing 100 μg/ml denatured salmon sperm DNA and 5–20×10$^6$ cpm of $^{32}$P-labeled probe. Washing of filters is done at 37° C. for 1 hour in a solution containing 2×SSC, 0.1% SDS. This is followed by a wash in 0.1×SSC, 0.1% SDS at 50° C. for 45 minutes before autoradiography. Other procedures using conditions of high stringency would include, for example, either a hybridization step carried out in 5×SSC, 5×Denhardt's solution, 50% formamide at 42° C. for 12 to 48 hours or a washing step carried out in 0.2×SSPE, 0.2% SDS at 65° C. for 30 to 60 minutes.

Probes are composed of nucleic acids or derivatives thereof such as modified nucleic acid and peptide nucleic acid. Modified nucleic acid includes nucleic acid with one or more altered sugar groups, altered internucleotide linkages, and/or altered nucleotide purine or pyrimidine bases. References describing modified nucleic acid include WO 98/02582, U.S. Pat. No. 5,859,221 and U.S. Pat. No. 5,852,188, each of which are hereby incorporated by reference herein.

Recombinant Expression

HG67 polypeptides can be expressed from recombinant nucleic acid in a suitable host or in a test tube using a translation system. Recombinantly expressed HG67 polypeptides are preferably used in assays to screen for compounds that bind to HG67 and modulate the activity of the receptor.

Preferably, expression is achieved in a host cell using an expression vector. An expression vector contains recombinant nucleic acid encoding for a polypeptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

A "recombinant nucleotide sequence" is a sequence that is present on a nucleic acid containing one or more nucleic acid regions not naturally associated with that sequence. Examples of such regions that may be present include one or more regulatory elements not naturally associated with the sequence, viral elements, and selectable markers.

Generally, the regulatory elements that are present in an expression vector include a transcriptional promoter, a ribosome binding site, a terminator, and an optionally present operator. Another preferred element is a polyadenylation signal providing for processing in eukaryotic cells. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Expression vectors providing suitable levels of polypeptide expression in different hosts are well known in the art. Mammalian expression vectors well known in the art include pcDNA3 (Invitrogen), pMC1neo (Stratagene), pXT1 (Stratagene), pSG5 (Stratagene), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUC-Tag (ATCC 37460), pCI-neo (Promega) and .lambda.ZD35 (ATCC 37565). Bacterial expression vectors well known in the art include pET11a (Novagen), lambda gt11 (Invitrogen), pcDNAII (Invitrogen), and pKK223-3 (Pharmacia). Fungal cell expression vectors well known in the art include pYES2 (Invitrogen), Pichia expression vector (Invitrogen). Insect cell expression vectors well known in the art include Blue Bac III (Invitrogen).

Recombinant host cells may be prokaryotic or eukaryotic. Examples of recombinant host cells include the following: bacteria such as *E. coli*; fungal cells such as yeast; mammalian cells such as human, bovine, porcine, monkey and rodent; and insect cells such as Drosophila and silkworm derived cell lines. Commercially available mammalian cell lines include L cells L-M(TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

To enhance expression in a particular host it may be useful to modify the sequence provided in SEQ. ID. NO. 2 to take into account codon usage of the host. Codon usage of different organisms are well known in the art. (See, Ausubel, *Current Protocols in Molecular Biology*, John Wiley, 1987–1998, Supplement 33 Appendix 1C.)

Expression vectors may be introduced into host cells using standard techniques. Examples of such techniques include transformation, transfection, lipofection, protoplast fusion, and electroporation.

Nucleic acid encoding for a polypeptide can be expressed in a cell without the use of an expression vector employing, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection.

Modulating HG67 Expression

HG67 expression can be modulated as a means for increasing or decreasing HG67 activity. Such modulation includes inhibiting HG67 nucleic acid activity to reduce HG67 expression or supplying HG67 nucleic acid to increase HG67 activity.

Inhibition of HG67 Activity

HG67 nucleic acid activity can be inhibited using nucleic acids recognizing HG67 nucleic acid and affecting the ability of such nucleic acid to be transcribed or translated. Inhibition of HG67 nucleic acid activity can be used, for example, in target validation studies.

A preferred target for inhibiting HG67 translation is mRNA. The ability of mRNA encoding HG67 to be translated into a protein can be effected by compounds such as anti-sense nucleic acid and enzymatic nucleic acid.

Anti-sense nucleic acid can hybridize to a region of a target mRNA. Depending on the structure of the anti-sense nucleic acid, anti-sense activity can be brought about by different mechanisms such as blocking the initiation of translation, preventing processing of mRNA, hybrid arrest, and degradation of mRNA by RNAse H activity.

Enzymatic nucleic acid can recognize and cleave another nucleic acid molecule. Preferred enzymatic nucleic acids are ribozymes.

General structures for anti-sense nucleic acids and ribozymes, and methods of delivering such molecules, are well known in the art. Modified and unmodified nucleic acids can be used as anti-sense molecules and ribozymes. Different types of modifications can effect certain anti-sense activities such as the ability to be cleaved by RNAse H, and can effect nucleic acid stability. Examples of references describing different anti-sense molecules and ribozymes, and the use of such molecules, are provided in U.S. Pat. Nos. 5,849,902, 5,859,221, and 5,852,188, which are each hereby incorporated by reference herein.

Guidelines for pharmaceutical administration in general are provided in, for example, *Remington's Pharmaceutical Sciences* 18$^{th}$ Edition, supra, and *Modern Pharmaceutics* 2$^{nd}$ Edition, supra. Nucleic acid can be introduced into cells present in different environments using in vitro, in vivo, or ex vivo techniques.

Increasing HG67 Expression

Nucleic acid coding for the HG67 can be used, for example, to cause an increase in weight or to create a test system (e.g., a transgenic animal) for screening for compounds affecting HG67 expression. Nucleic acids can be introduced and expressed in cells present in different environments.

Guidelines for pharmaceutical administration in general are provided in, for example, *Remington's Pharmaceutical Sciences* 18$^{th}$ Edition, supra. and *Modern Pharmaceutics* 2$^{nd}$ Edition, supra. Examples of techniques useful in gene therapy are illustrated in *Gene Therapy & Molecular Biology: From Basic Mechanisms to Clinical Applications*, Ed. Boulikas, Gene Therapy Press, 1998 (hereby incorporated by reference herein).

Modulating HG67 Activity

Using the present application as a guide compounds able to modulate HG67 can be obtained and used to achieve a beneficial effect in a patient. Such effects can be obtained, for example, by altering weight or relieving stress using a compound active at HG67.

Altering weight is particularly useful for gaining weight in an under weight patient or losing weight in an over weight patient. In addition, for example, farm animals can be treated to gain weight. Under weight patients include those having a body weight about 10% or less, 20% or less, or 30% or less, than the lower end of a "normal" weight range or Body Mass Index ("BMI"). Over weight patients include those having a body weight about 10% or more, 20% or more, 30% or more, or 50% or more, than the upper end of a "normal" weight range or BMI. "Normal" weight ranges are well known in the art and take into account factors such as a patient age, height, and body type.

BMI measures your height/weight ratio. It is determined by calculating weight in kilograms divided by the square of height in meters. The BMI "normal" range is 19–22.

Preferably, HG67 activity is altered using a non-protein HG67 agonist or antagonist. Agonist and antagonists are preferably organic compounds comprising one or more aryl or heteroaryl and having a molecule weight between about 150 and 900.

HG67 modulating compounds can be provided in kit. Such a kit typically contains an active compound in dosage forms for administration. A dosage form contains a sufficient amount of active compound such that a beneficial effect can be obtained when administered to a patient during regular intervals, such as 1 to 6 times a day, during the course of 1 or more days. Preferably, a kit contains instructions indicating the use of the dosage form for weight reduction (e.g., to treat obesity or overweight) or stress reduction, and the amount of dosage form to be taken over a specified time period.

Dosing for Therapeutic Applications

Guidelines for pharmaceutical administration in general are provided in, for example, *Remington's Pharmaceutical Sciences* 18$^{th}$ Edition, Ed. Gennaro, Mack Publishing, 1990, and *Modern Pharmaceutics* 2$^{nd}$ Edition, Eds. Banker and Rhodes, Marcel Dekker, Inc., 1990, both of which are hereby incorporated by reference herein.

HG67 active compounds having appropriate functional groups can be prepared as acidic or base salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

HG67 active compounds can be administered using different routes including oral, nasal, by injection, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

When administered by nasal aerosol or inhalation, compositions can be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds may also be administered in intravenous (both bolus and infusion), intraperitoneal, subcutaneous, topical with or without occlusion, or intramuscular form, all using forms well known to those of ordinary skill in the pharmaceutical arts. When administered by injection, the injectable solutions or suspensions may be formulated using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Suitable dosing regimens for the therapeutic applications of the present invention are selected taking into account factors well known in the art including age, weight, sex and medical condition of the patient; the severity of the condition to be treated; the route of administration; the renal and hepatic function of the patient; and the particular compound employed. Guidelines for pharmaceutical administration and pharmaceutical compositions are provided in, for example, *Remington's Pharmaceutical Sciences* 18$^{th}$ Edition, supra. and *Modern Pharmaceutics* 2$^{nd}$ Edition, supra.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a patient is expected to be between 0.01 and 1,000 mg per adult patient per day.

EXAMPLES

Examples are provided below to further illustrate different features and advantages of the present invention. The examples also illustrate useful methodology for practicing the invention. These examples do not limit the claimed invention.

Example 1

Cloning HG67

The full-length coding sequence of HG67 was cloned using the strategy and procedures described previously by McDonald, et al. 1998. *Biochem. Biophys. Res. Commun.*, 247, 266–270. Pooled cDNA libraries of fetal brain, testis, placenta, and prostate were used for the cloning. The following primers were used for PCR and sequencing reactions:

SEQ. ID. NO. 15 CTGACATCTATATCTGCAACCTGG
SEQ. ID. NO. 16 TGCAGAGAGGCCCCCAAACACCC
SEQ. ID. NO. 17 TGTGGCTGATTTGGTCCAC
SEQ. ID. NO. 18 CCTCGGGCCCATTGGTGAATAAG
SEQ. ID. NO. 19 TTGTGTGGAATTGTGAGCGGATAAC
SEQ. ID. NO. 20 CCCAGGCTTTACACTTTATGCTTCC
SEQ. ID. NO. 21 GGGGATGTGCTGCAAGGCGA
SEQ. ID. NO. 22 CCAGGGTTTTCCCAGTCACGAC.

PCR reactions were carried out using SEQ. ID. NO. 15 and SEQ. ID. NO. 16 primers to screen superpools of arrayed cDNA libraries. Positive pools were identified.

PCR-based race reactions were carried out using vector and gene-specific primers as follows: SEQ. ID. NO. 15+SEQ. ID. NO. 21 (vector primer) or SEQ. ID. NO. 20 (vector primer), and SEQ. ID. NO. 16+SEQ. ID. NO. 21 or SEQ. ID. NO. 20. The PCR products from these reactions (primary reaction) were used as templates to carry out secondary PCR reactions using primers nested within the primary reactions, i.e., SEQ. ID. NO. 17 (inside of SEQ. ID. NO. 15)+SEQ. ID. NO. 22 (vector primer) or SEQ. ID. NO. 19 (vector primer) for templates from SEQ. ID. NO. 15-containing primary reactions, and SEQ. ID. NO.18 (inside of SEQ. ID. NO. 16)+SEQ. ID. NO. 22 or SEQ. ID. NO. 19 for templates from SEQ. ID. NO.16-containing primary reactions.

Amplified products were purified and sequenced using M13 forward and reverse primers, and the SEQ. ID. NO. 17 and SEQ. ID. NO. 18 primers. The sequences were analyzed and assembled, resulting in the identification of an open reading frame of 1023 nucleotides encoding a polypeptide of 340 amino acids and a stop codon. A full-length clone was obtained by PCR from a fetal brain library.

HG67 Amino Acid Sequence (SEQ. ID. NO. 1)

MNPFHASCWNTSAELLNKSWNKE-
FAYQTASVVDTVILPSMIGIICSTGLVG-
NILIVFTIIRSRKKTVPDIYICNLA-
VADLVHIVGMPFLIHQWARGGEWVFGGPLCTIIT
SLDTCNQFACSAIMTVMSVDRYFALVQP-
FRLTRWRTRYKTIRINLGLWAASFILA-
LPVWVYSKVIKFKDGVESCAFDLTSPD-
DVLWYTLYLTITTFFFPLPLILVCYILILCYTWEMYQQ
NKDARCCNPSVPKQRVMKLTKMVLVLV-
VVFILSAAPYHVIQLVNLQMEQPT-
LAFYVGYYLSICLSYASSSINPFLY-
ILLSGNFQKRLPQIQRRATEKEINNMGNTLKSHF

HG67 cDNA Sequence (SEQ. ID. NO. 2)

ATGAATCCATTTCATGCATCTTGTTG-
GAACACCTCTGCCGAACTTTTAAA-
CAAATCCTGGAATAAAGAGTTTGCTTAT-
CAAACTGCCAGTGTGGTAGATACAGTCATCCTCCC
TTCCATGATTGGGATTATCTGTTCAA-
CAGGGCTGGTTGGCAACATCCTCATTG-
TATTCACTATAATAAGATCCAG-
GAAAAAAACAGTCCCTGACATCTATATCTGCAACC
TGGCTGTGGCTGATTTGGTCCACATAGT-
TGGAATGCCTTTTCTTATTCAC-
CAATGGGCCCGAGGGGGAGAGTGGGT-
GTTTGGGGGGCCTCTCTGCACCATCATCACATCCC
TGGATACTTGTAACCAATTTGCCTG-
TAGTGCCATCATGACTGTAATGAGTGTG-
GACAGGTACTTTGCCCTCGTCCAAC-
CATTTCGACTGACACGTTGGAGAACAAGGTACAA
GACCATCCGGATCAATTTGGGC-
CTTTGGGCAGCTTCCTTTATCCTGGCAT-
TGCCTGTCTGGGTCTACTCGAAGGTCAT-
CAAATTTAAAGACGGTGTTGAGAGTTGTGCTTTTG
ATTTGACATCCCCTGACGATGTACTCTG-
GTATACACTTTATTTGACGATAA-
CAACTTTTTTTTCCCTCTACCCT-
TGATTTTGGTGTGCTATATTTTAATTTTATGCTATAC
TTGGGAGATGTATCAACAGAATAAGGAT-
GCCAGATGCTGCAATCCCAGTGTAC-
CAAAACAGAGAGTGATGAAGTTGACAAA-
GATGGTGCTGGTGCTGGTGGTAGTCTTTATCCTGA
GTGCTGCCCCTTATCATGTGATA-
CAACTGGTGAACTTACAGATGGAACAGC-
CCACACTGGCCTTCTATGTGGGTTAT-
TACCTCTCCATCTGTCCAGCTATGCCAGCAGCA
GCATTAACCCTTTTCTCTACATCCTGCT-
GAGTGGAAATTTCCAGAAACGTCTGCCT-
CAAATCCAAAGAAGAGCGACTGAGAAG-
GAAATCAACAATATGGGAAACACTCTGAAATCAC
ACTTTTAG

Example 2

Transient Expression of HG67

The entire coding sequence of human HG67 was cloned into BamHI -NotI site of pEF1/V5-HisB plasmid vector (Invitrogen, Carlsbad, Calif.). The resultant construct was transfected into HEK-293T cells using Effectene (Qiagen, Hilden, Germany) or LipofectAmine PLUS (Life Technologies) according to the manufacture's instructions. Human embryonic kidney cells constitutively expressing SV40 large T antigen (HEK-293T) were maintained in D-MEM/F-12 medium (Life Technologies, Rockville, Md.) supplemented with 10% fetal bovine serum, 100 units/ml penicillin-G and 100 μg/ml streptomycin at 37° C. with 5% $CO_2$ in a humidified atmosphere.

The intracellular calcium ion concentration ($[Ca^{2+}]_i$) was measured fluorometrically using a $Ca^{2+}$-sensitive fluorescent dye, fura-2. HEK293T cells transiently transfected with pEF1/V5-HisB plasmid vector harboring HG67 cDNA were harvested by phosphate-buffered saline containing 2 mM EDTA 48 hours after transfection, and washed once with the assay buffer (Hanks' balanced salt solution, 10 mM HEPES, 0.1% BSA, pH 7.4). The cells were suspended with the buffer containing 2 μM fura-2 acetoxymethylester (Dojin, Kumamoto, Japan) into the cell density of $1.0 \times 10^7$ cells/ml and incubated at 37° C. for 60 minutes with gently shaking. The fura-2-loaded cells were washed twice with the buffer and re-suspended with the buffer to $1.0 \times 10^6$ cells/ml. 0.5 ml of the resultant suspension was stirred continuously at 37° C. in a glass cuvette during the measurement. Five microliters of dimethyl sulfoxide (DMSO) solution of MCH (Peptide Institute, Osaka, Japan) or [Phe[13], Leu[19]]-MCH (Neosystem Laboratories, Strasbourg, France) was added into the cell suspension, and fluorescent intensity at an emission wavelength of 500 nm and excitation wavelengths of 340 and 380 nm was monitored with a CAF-110 intracellular ion analyzer (JASCO, Tokyo, Japan).

As shown in FIG. 3, both MCH and [Phe[13], Leu[19]]-MCH dose-dependently caused increase in intracellular calcium levels in the HEK293T cells transiently expressing HG67 with potent efficacy ($EC_{50}$ of MCH and [Phe[13], Leu[19]]-MCH were calculated as 20 and 78 pM, respectively), but failed to induce detectable $[Ca^{2+}]_i$ increase in the non-transfected cells (data not shown). These results confirm that HG67 is an MCH receptor and can be designated MCH-R2.

Example 3

MCH Binding Experiments

HEK293T cells were seeded into 24-well culture plates coated with poly-L-Lys at $1 \times 10^5$ cells/well and were cultured during over-night. The adherent cells were transfected with pEF1/V5-HisB/MCH-2R plasmid (see Example 2). Forty-eight hours after transfection, the transfected monolayer cells were rinsed with M-MEM/F-12 medium containing 10% fetal bovine serum, 15 mM HEPES and 0.1% bacitracin. The cells were then incubated in 220 µl/ well of the same medium with [$^{125}$I]-MCH (100 pM, NEN Life Science Products, Boston, Mass.) for 30 minutes at 37° C. After the incubation, the cells were washed three times with the ice cold medium and lysed with 500 µl/well of 2 M NaOH. The lysates were transferred into test tubes and the cell-bound radioactivity was measured by a COBLA Quantum γ-counter (Packard Instrument, Meriden, Conn.). Nonspecific binding was defined in the presence of 1 µM cold MCH.

[$^{125}$I]-MCH bound to the HEK293T cells expressing HG67 with a good window, whereas any specific binding was not observed into mock transfected cells (Table 1).

TABLE 1

|  | Total binding (DMSO) Cpm | | Nonspecific binding (1 µM MCH) Cpm | |
|---|---|---|---|---|
| HG67 | 8546.9 | 9653.5 | 367.6 | 543.5 |
| Mock | 516.4 | 392.5 | 352.2 | 326.6 |

Example 4

Activation of HG67 by MCH in HEK/293/aeq17/Gα15

The complete coding sequence of HG67 cloned in pCR3.1. (Invitrogen, Carlsbad, Calif., USA), was subcloned into pIRESpuromycin (Clontech, Inc., Palo Alto, Calif., USA). Clones were confirmed by DNA sequencing.

The HEK293/aeq17 cell line was employed to measure activity. (Button and Brownstein, 1993, *Cell Calcium*, 14:663–671.) The complete coding sequence of mouse promiscuous G protein Gα15 was cloned into the vector pIRES/zeocin (Clontech, Palo Alto, Calif., USA). The resulting plasmid was transfected into HEK293/aeq17 cells using Lipofectamine (GIBCO-BRL, Gaithersburg, Md., USA) and selected with zeocin. Individual stable colonies were isolated and tested for coupling of various receptors. A clone showing promiscuous coupling was named HEK293/aeq17/Gα15 and used in subsequent assays.

HEK/293/aeq17/Gα15 were grown in Dulbecco's Modified Medium (DMEM, GIBCO-BRL, Gaithersburg, Md., USA) +10% fetal bovine serum (heat inactivated), 1 mM sodium pyruvate, 500 µg/ml Geneticin, 200 µg/ml zeocin, 100 µg/ml streptomycin, 100 units/ml penicillin. Plasmid DNA of HG67 and MCH-R1, were transfected into HEK293/aeq17/Gα15 using Lipofectamine-2000 (Gaithersburg, Md., USA) following the conditions suggested by GIBCO-BRL. Two days after transfection, cells were washed once with DMEM+0.1% fetal bovine serum, and then charged for one hour at 37° C./5% $CO_2$ in DMEM containing 8 µM coelenterazine cp (Molecular Probes, Eugene, Oreg., USA) and 30 µM glutathione. The cells were then washed once with Versene (GIBCO-BRL, Gaithersburg, Md., USA), detached using Enzyme-free cell dissociation buffer (GIBCO-BRL, Gaithersburg, Md., USA), diluted into ECB (Ham's. F12 nutrient mixture (GIBCO-BRL)+0.3 mM $CaCl_2$, 25 mM HEPES, pH7.3, 0.1% fetal bovine serum). The cell suspension was centrifuged at 500×g for 5 minutes. The supernatant was removed, and the pellet was resuspended in 10 mL ECB. The cell density was determined by counting with a hemacytometer and adjusted to 500,000 cells/ml in ECB.

Figure 4:
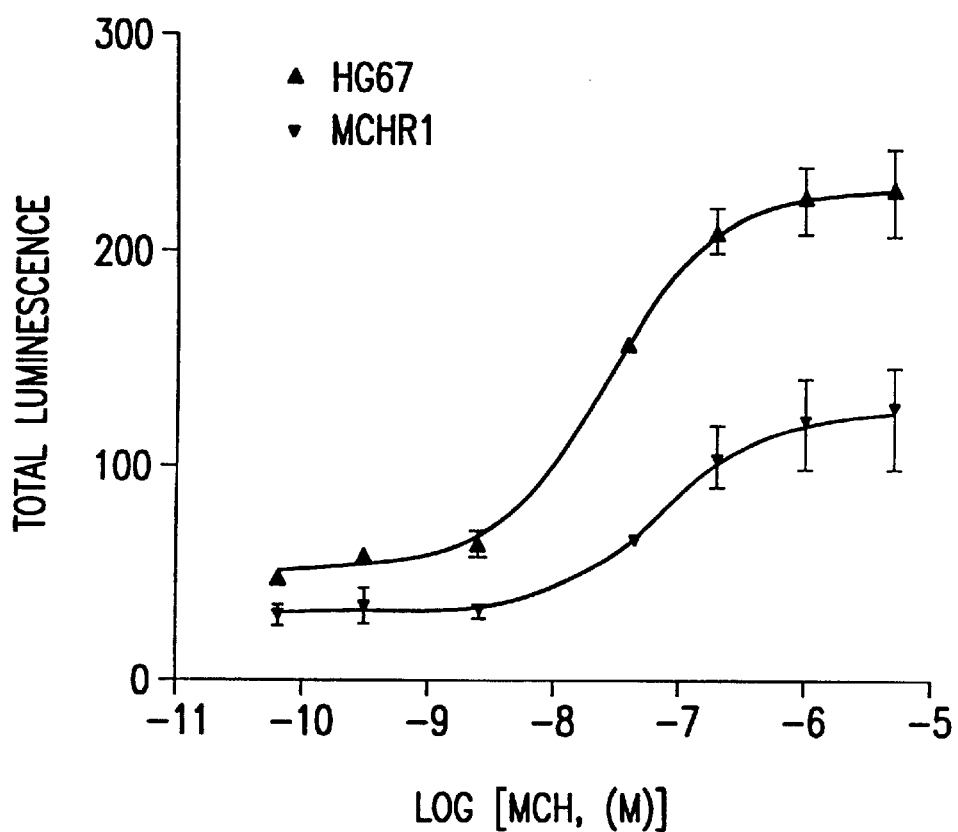
FIG. 4 illustrates activation of HG67 by human MCH in the aequorin assay. HEK293/seq17/$G_\alpha 15$ cells were transfected with HG67 or vector only and then assayed against MCH two days post transfection. RLU: random luminescence units. The $EC_{50}$ of MCH for HG67 and MCH-R1 is 26 nM and 66 nM, respectively in these cells.

Human MCH was diluted in ECB into 2× concentrates using 5-fold serial dilutions, and aliquoted into assay plates in triplicates at 0.1 ml/well. The cell suspension was injected at 0.1 ml/well, read and integrated for a total of 400 readings using a luminometer (Luminoskan Ascent, Labsystems Oy, Helsinki, Finland). Data were analyzed using the software GraphPad Prism Version 3.0 (GraphPad Software, Inc., San Diego, Calif., USA). As shown in FIG. 4, both HG67 and MCH-R1-transfected cells showed a robust, dose-dependent response to human MCH. The $EC_{50}$ in this assay of MCH for HG67 and MCH-R1 is 26 nM and 66 nM, respectively.

Example 5

Activation of HG67 by MCH in HEK/293/aeq17

Measurement of HG67 expression using the aequorin-expressing stable reporter cell line 293-AEQ17 was performed employing a Luminoskan RT luminometer (Labsystems Inc., Gaithersburg, Md.). 293-AEQ17 cells ($8 \times 10^5$ cells plated 18 hours before transfection in a T75 flask) were transfected with 22 µg human HG67/pIRESpuro plasmid DNA:264 µg lipofectamine.

Figure 5:
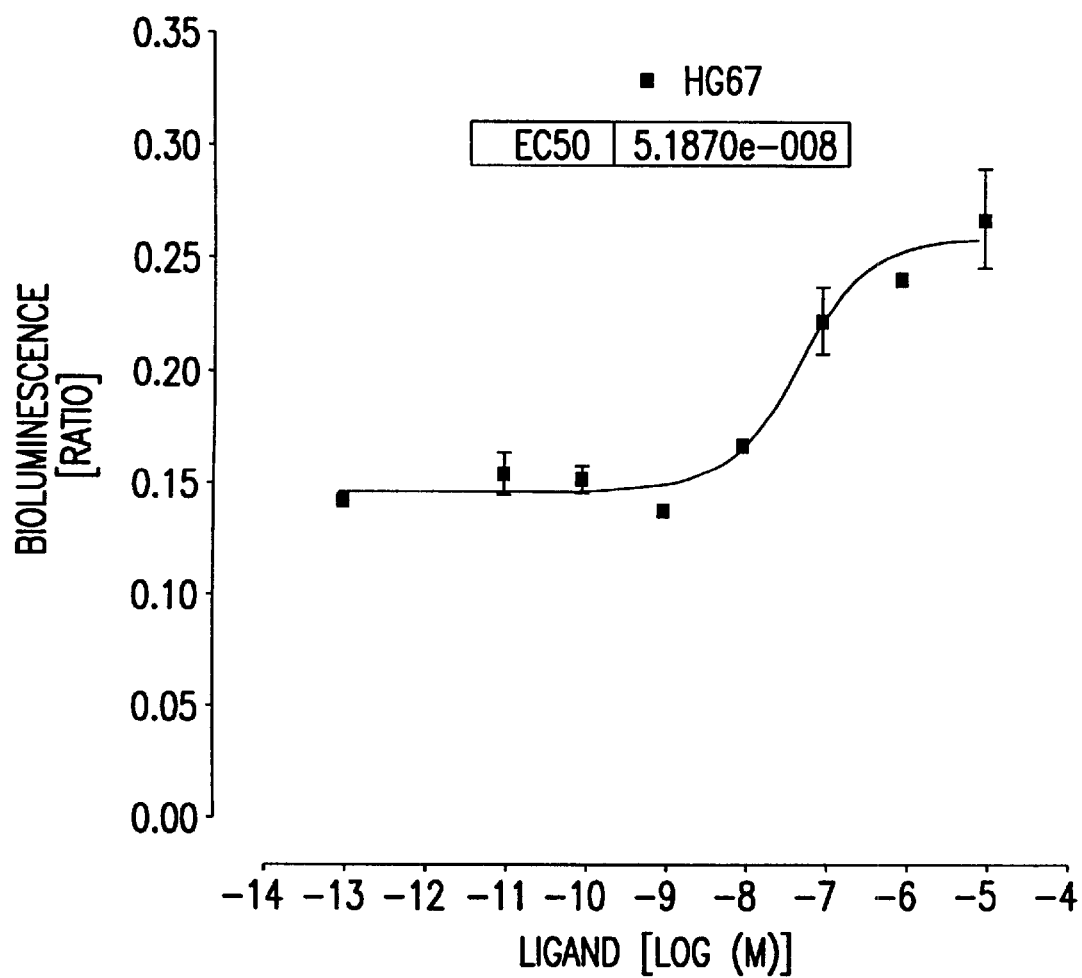
FIG. 5 illustrate expression of HG67 and activation by MCH in HEK-293/aeq/17 cells.

Following approximately 40 hours of expression the apo-aequorin in the cells was charged for 4 hours with coelenterazine (10 µM) under reducing conditions (300 mM reduced glutathione) in ECB buffer (140 mM NaCl, 20 mM KCl, 20 mM HEPES-NaOH [pH=7.4], 5 mM glucose, 1 mM $MgCl_2$, 1 mM $CaCl_2$, 0.1 mg/ml bovine serum albumin). The cells were harvested, washed once in ECB medium and resuspended to 500,000 cells/ml. 100 ml of cell suspension (corresponding to $5 \times 10^4$ cells) was then injected into the test plate, and the integrated light emission was recorded over 30 seconds, in 0.5 second units. 20 µL of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton X-100 lysis response. Results are shown in FIG. 5.

Example 6

Membrane Binding Assays

Membrane binding assays were performed on transiently-transfected COS-7 cells using MCH-R2 in the plasmid vector pCIneo, or on a CHO line stably expressing MCH-R2 in the plasmid vector pEF1/V5-HisB. For transient expression, COS-7 cells were cultured in Dulbecco's modified Eagle medium (Gibco BRL) with 10% heat inactivated fetal calf serum.

A suspension of $7 \times 10^6$ COS-7 cells were transfected with 20 µg of pCIneo/MCH-R2 plasmid by electroporation (Strader, et al., 1987. *Proc. Natl. Acad. Sci. U.S.A.* 84(13), 4384–8), and cells were harvested after 60–72 hours. Membranes were prepared from transient and stable transfectants by hypotonic lysis, frozen in liquid nitrogen, and stored at −80° C. as described (MacNeil, et al., 1994. *Biochem. Biophys. Res. Commun.* 198, 328–334).

A scintillation proximity assay (SPA) was developed to measure the specific binding of [$^{125}$I]Phe$^{13}$Tyr$^{19}$-MCH (~2000 Ci/mmol; NEN Life Sciences, Boston, Mass.) to MCH-R1 and MCH-R2 containing membranes. SPA was carried out using wheat-germ agglutinin-polyvinyltoluene beads (Amersham Corp., Arlington Heights, Ill.), in 96-well OptiPlates (Packard, Meriden, Conn.). Each well contained 0.25 mg of SPA beads, 1–10 μg of membrane protein, and 200 μl of binding buffer. Binding buffer contained 50 mM Tris pH 7.4, 8 mM MgCl$_2$, 12% glycerol, 0.1% BSA (Sigma, St. Louis, Mo.) and protease inhibitors (4 μg/ml of leupeptin (Sigma, St. Louis, Mo.), 40 μg/ml of Bacitracin (Sigma, St. Louis, Mo.), 5 μg/ml of Aprotinin (Roche Molecular Biochem., Indianapolis, Ind.), and 100 μM AEBSF (Roche Molecular Biochem., Indianapolis, Ind.)).

Assays were optimized with respect to membrane preparations: for CHO/MCH-R1 membranes, 1 μg of membranes per well yielded a >6× specific binding window and for COS or CHO MCH-R2 membranes, 8 μg of membrane protein yielded a window of about 3×. Specific binding is defined as the difference between total binding and non-specific binding conducted in the presence of 500 nM unlabeled MCH.

Beads were coated with membranes for 20 minutes and dispensed to the 96 wells, various concentrations of test compounds in DMSO were added (final DMSO concentration 1%–2%), then 25 nCi of [$^{125}$I]Phe$^{13}$Tyr$^{19}$-MCH was added to the wells. After equilibrating at room temperature for 3 hours, the plates were read in a TopCount (Packard, Meriden, Conn.). IC$_{50}$ calculations were performed using Prism 3.0 (GraphPad Software, San Diego, Calif.).

Human MCH as well as (Phe$^{13}$Tyr$^{19}$)-MCH and salmon MCH displaced iodinated (Phe$^{13}$Tyr$^{19}$)-MCH radioligand with low- and sub-nanomolar half-maximal inhibition (IC$_{50}$) concentrations (Table 2).

TABLE 2

| Ligand | Binding (IC50) | | Function (EC50) | |
|---|---|---|---|---|
|  | MCH-R1 | MCH-R2 | MCH-R1 | MCH-R2 |
| MCH | 0.3 | 1.5 | 35.4 | 44.1 |
| (Phe$^{13}$Tyr$^{19}$)MCH | 0.3 | 0.8 | 83.1 | 65.5 |
| Salmon MCH | 0.2 | 436.7 | 119.2 | 90.5 |

Example 7

Additional Experiments

Additional experiments were preformed to further characterize MCH-R2 activity and determine the location of MCH-R2. Salmon MCH activates MCH-R2, albeit with a lower potency than human MCH, as measured in an aequorin assay performed along the lines described in Example 5.

MCH-R2 appears to activate Gαq. MCH very potently stimulated IP turnover through MCH-R2. MCH-R2 displayed an EC$_{50}$ of 2.8 nM while MCH-R1 showed an EC$_{50}$ of about 90 nM. Intracellular calcium mobilization through MCH-R2 was not affected by different concentrations of pertussis toxin (PTX), while MCH-R1 signaling was reduced in a dose dependent manner to about 50%. The results of incomplete PTX-inhibition of MCH-R1 signaling is in contrast to Lembo, et al., 1999. *Nat Cell Biol.* 1(5), 267–71, who found complete PTX inhibition of MCH-1R signaling and might be attributed to different expression levels of recombinant receptor. A recent report indicates a PTX insensitive MCH response in insulin producing cells such as CRI-G1 and RINm5F. (Tadayyon, et al., 2000. 275(2), 709–712).

Northern blot analysis and in situ hybridization indicate that MCH-R2 is specifically expressed in the brain. Within the brain, high levels of MCH-R2 were detected in the cerebral cortex, hippocampus, and hypothalamus. Other areas of expression included caudate nucleus, putamen and thalamus.

Other embodiments are within the following claims. While several embodiments have been shown and described, various modifications may be made without departing from the spirit and scope of the present invention.

What is claimed:

1. A purified nucleic acid comprising a nucleotide sequence encoding a polypeptide comprising the amino acid sequence of SEQ ID NO: 1.

2. The purified nucleic acid of claim 1, wherein said nucleic acid comprises the sequence of SEQ ID. NO: 2.

3. The purified nucleic acid of claim 1, wherein said polypeptide consists of SEQ ID NO: 1.

4. An expression vector comprising a nucleotide sequence encoding a polypeptide comprising the amino acid sequence of SEQ ID NO: 1, wherein said nucleotide sequence is transcriptionally coupled to an exogenous promoter.

5. The expression vector of claim 4, wherein said polypeptide consists of the amino acid sequence of SEQ ID NO: 1.

6. The expression vector of claim 4, wherein said nucleotide sequence comprises the sequence of SEQ ID NO: 2.

7. The expression vector of claim 4, wherein said nucleotide sequence consists of the sequence of SEQ ID NO: 2.

8. A recombinant cell comprising the expression vector of claim 4, wherein said cell comprises an RNA polymerase recognized by said promoter.

9. A recombinant cell made by a process comprising the step of introducing the expression vector of claim 4 into said cell.

10. A method of preparing a melanin-concentrating hormone receptor polypeptide comprising the step of growing the recombinant cell of claim 8 under conditions wherein said polypeptide is expressed from said expression vector.

11. A recombinant cell comprising the expression vector of claim 4.

12. A recombinant cell comprising the expression vector of claim 5.

13. A recombinant cell comprising the expression vector of claim 6.

14. A recombinant cell comprising the expression vector of claim 7.

* * * * *

SEQUENCE LISTING

<160> NUMBER OF SEQ ID NOS: 22

<210> SEQ ID NO 1
<211> LENGTH: 340
<212> TYPE: PRT
<213> ORGANISM: Human

<400> SEQUENCE: 1

Met Asn Pro Phe His Ala Ser Cys Trp Asn Thr Ser Ala Glu Leu Leu
1               5                   10                  15

Asn Lys Ser Trp Asn Lys Glu Phe Ala Tyr Gln Thr Ala Ser Val Val
            20                  25                  30

-continued

```
Asp Thr Val Ile Leu Pro Ser Met Ile Gly Ile Ile Cys Ser Thr Gly
            35                  40                  45

Leu Val Gly Asn Ile Leu Ile Val Phe Thr Ile Ile Arg Ser Arg Lys
        50                  55                  60

Lys Thr Val Pro Asp Ile Tyr Ile Cys Asn Leu Ala Val Ala Asp Leu
 65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Arg Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Val Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Ala Thr Glu Lys Glu Ile Asn Asn Met Gly Asn Thr Leu
                325                 330                 335

Lys Ser His Phe
            340

<210> SEQ ID NO 2
<211> LENGTH: 1023
<212> TYPE: DNA
<213> ORGANISM: Human

<400> SEQUENCE: 2
atgaatccat tcatgcatc  ttgttggaac acctctgccg aacttttaaa caaatcctgg      60
aataaagagt tgcttatca  aactgccagt gtggtagata cagtcatcct cccttccatg    120
attgggatta tctgttcaac agggctggtt ggcaacatcc tcattgtatt cactataata    180
agatccagga aaaaaacagt ccctgacatc tatatctgca acctggctgt ggctgatttg    240
gtccacatag ttggaatgcc ttttcttatt caccaatggg cccgaggggg agagtgggtg    300
tttggggggc ctctctgcac catcatcaca tccctggata cttgtaacca atttgcctgt    360
```

-continued

```
agtgccatca tgactgtaat gagtgtggac aggtactttg ccctcgtcca accatttcga      420
ctgacacgtt ggagaacaag gtacaagacc atccggatca atttgggcct ttgggcagct      480
tcctttatcc tggcattgcc tgtctgggtc tactcgaagg tcatcaaatt taaagacggt      540
gttgagagtt gtgcttttga tttgacatcc cctgacgatg tactctggta tacactttat      600
ttgacgataa caactttttt tttccctcta cccttgattt tggtgtgcta tattttaatt      660
ttatgctata cttgggagat gtatcaacag aataaggatg ccagatgctg caatcccagt      720
gtaccaaaac agagagtgat gaagttgaca agatggtgc tggtgctggt ggtagtcttt      780
atcctgagtg ctgcccctta tcatgtgata caactggtga acttacagat ggaacagccc      840
acactggcct tctatgtggg ttattacctc tccatctgtc tcagctatgc cagcagcagc      900
attaaccctt ttctctacat cctgctgagt ggaaatttcc agaaacgtct gcctcaaatc      960
caaagaagag cgactgagaa ggaaatcaac aatatgggaa acactctgaa atcacacttt     1020
tag                                                                   1023
```

<210> SEQ ID NO 3
<211> LENGTH: 925
<212> TYPE: DNA
<213> ORGANISM: Human
<220> FEATURE:
<221> NAME/KEY: misc_feature
<222> LOCATION: (1)...(925)
<223> OTHER INFORMATION: n = A,T,C or G

<400> SEQUENCE: 3

```
gcttggatcg ggaacgaatt cattctttgt ttctaatata ccctggtttt gtgattttt       60 tttcttgcac tgaattgcaa ataaaactga gtcaaaaaga atgattagaa aaaggagat      120 ttttgtgttt tatgttttcc attaaaaata ttcctctgtg aaagttgaac aaaatattct      180
taagtaatca gttctacagt gaaacaaagg aagaaaacct ctgctgttat aaaccaaaac      240
tggtgttgga attggaatga gcttggggaa gcacaggcac ctctgaatta tattaagata      300
tttcaaagtc tttcacttac ctgtccacac tcattacagt catgatggca ctacaggcaa      360
attggttaca agtatccagg gatgtgatga tggtgcagag aggcccccca acacccact      420 ctccccctcg ggcccattgg tgaataagaa aaggcattcc aactatgtgg accaaatcag      480
ccacagccag gttgcagata tagatgtcag ggactgtttt tttcctggat ctgaaagaga      540
tagaggaaac tgaggattga cattgaatgt gtacagacta ttcgatatat gctacctcat      600
acacaatttt taattgacat tatgcgtttt taaatggtaa aggagaaccc tttcccattg      660
ccttaaagga cttcgccnnc ctgggggtgt tttaaagcat ttggaccaat ttatttgata      720
actactgggg gggttaaaaa tatgtccaca aatatttgat attcccttca gtaggtggag      780
cctaattccc tctgagtgct gaccttatta acttgctcta acaatgagat ttgggcgaag      840
tgcagggtgt gactttaaat aagtacaaat ttttgggggc ttctcttgtc tctgtggatt      900
gcttcctgag gagccgctca tctga                                            925
```

<210> SEQ ID NO 4
<211> LENGTH: 925
<212> TYPE: DNA
<213> ORGANISM: Artificial Sequence
<220> FEATURE:
<221> NAME/KEY: misc_feature
<222> LOCATION: (1)...(925)
<223> OTHER INFORMATION: n = A,T,C or G
<223> OTHER INFORMATION: Antisense sequence of Sequence ID. No. 3

-continued

```
<400> SEQUENCE: 4
tcagatgagc ggctcctcag gaagcaatcc acagagacaa gagaagcccc caaaaatttg      60
tacttattta aagtcacacc ctgcacttcg cccaaatctc attgttagag caagttaata     120
aggtcagcac tcagagggaa ttaggctcca cctactgaag ggaatatcaa atatttgtgg     180
acatattttt aaccccccca gtagttatca aataaattgg tccaaatgct ttaaaacacc     240
cccaggnngg cgaagtcctt taaggcaatg ggaaagggtt ctcctttacc atttaaaaac     300
gcataatgtc aattaaaaat tgtgtatgag gtagcatata tcgaatagtc tgtacacatt     360
caatgtcaat cctcagtttc ctctatctct ttcagatcca ggaaaaaaac agtccctgac     420
atctatatct gcaacctggc tgtggctgat tggtccaca tagttggaat gccttttctt     480
attcaccaat gggcccgagg gggagagtgg gtgtttgggg ggcctctctg caccatcatc     540
acatccctgg atacttgtaa ccaatttgcc tgtagtgcca tcatgactgt aatgagtgtg     600
gacaggtaag tgaaagactt tgaaatatct taatataatt cagaggtgcc tgtgcttccc     660
caagctcatc ccaattccaa caccagtttt ggtttataac agcagaggtt ttcttccttt     720
gtttcactgt agaactgatt acttaagaat attttgttca actttcacag aggaatattt     780
ttaatggaaa acataaaaca caaaaatctc cttttttcta atcattcttt ttgactcagt     840
tttatttgca attcagtgca agaaaaaaaa atcacaaaac cagggtatat tagaaacaaa     900
gaatgaattc gttcccgatc caagc                                           925

<210> SEQ ID NO 5
<211> LENGTH: 13
<212> TYPE: PRT
<213> ORGANISM: Artificial Sequence
<220> FEATURE:
<223> OTHER INFORMATION: MCH-R2 Segment

<400> SEQUENCE: 5

Met Asn Pro Phe His Ala Ser Cys Trp Asn Thr Ser Ala
 1               5                   10

<210> SEQ ID NO 6
<211> LENGTH: 11
<212> TYPE: PRT
<213> ORGANISM: Artificial Sequence
<220> FEATURE:
<223> OTHER INFORMATION: MCH-R2 Segment

<400> SEQUENCE: 6

Met Ile Gly Ile Ile Cys Ser Thr Gly Leu Val
 1               5                   10

<210> SEQ ID NO 7
<211> LENGTH: 14
<212> TYPE: PRT
<213> ORGANISM: Artificial Sequence
<220> FEATURE:
<223> OTHER INFORMATION: MCH-R2 Segment

<400> SEQUENCE: 7

Met Tyr Gln Gln Asn Lys Asp Ala Arg Cys Cys Asn Pro Ser
 1               5                   10

<210> SEQ ID NO 8
<211> LENGTH: 14
<212> TYPE: PRT
<213> ORGANISM: Artificial Sequence
```

```
<220> FEATURE:
<223> OTHER INFORMATION: MCH-R2 Segment

<400> SEQUENCE: 8

Met Val Leu Val Leu Val Val Val Phe Ile Leu Ser Ala Ala
 1               5                  10

<210> SEQ ID NO 9
<211> LENGTH: 16
<212> TYPE: PRT
<213> ORGANISM: Artificial Sequence
<220> FEATURE:
<223> OTHER INFORMATION: MCH-R2 Segment

<400> SEQUENCE: 9

Met Glu Gln Pro Thr Leu Ala Phe Tyr Val Gly Tyr Tyr Leu Ser Ile
 1               5                  10                  15

<210> SEQ ID NO 10
<211> LENGTH: 27
<212> TYPE: DNA
<213> ORGANISM: Artificial Sequence
<220> FEATURE:
<223> OTHER INFORMATION: MCH-R2 Nucleic Acid Segment

<400> SEQUENCE: 10
atgaatccat tcatgcatc ttgttgg                                          27

<210> SEQ ID NO 11
<211> LENGTH: 24
<212> TYPE: DNA
<213> ORGANISM: Artificial Sequence
<220> FEATURE:
<223> OTHER INFORMATION: MCH-R2 Nucleic Acid Segment

<400> SEQUENCE: 11
atgattggga ttatctgttc aaca                                            24

<210> SEQ ID NO 12
<211> LENGTH: 28
<212> TYPE: DNA
<213> ORGANISM: Artificial Sequence
<220> FEATURE:
<223> OTHER INFORMATION: MCH-R2 Nucleic Acid Segment

<400> SEQUENCE: 12
atgtatcaac agaataagga tgccagat                                        28

<210> SEQ ID NO 13
<211> LENGTH: 27
<212> TYPE: DNA
<213> ORGANISM: Artificial Sequence
<220> FEATURE:
<223> OTHER INFORMATION: MCH-R2 Nucleic Acid Segment

<400> SEQUENCE: 13
atgaagttga caaagatggt gctggtg                                         27

<210> SEQ ID NO 14
<211> LENGTH: 27
<212> TYPE: DNA
<213> ORGANISM: Artificial Sequence
<220> FEATURE:
<223> OTHER INFORMATION: MCH-R2 Nucleic Acid Segment

<400> SEQUENCE: 14
```

```
atgggaaaca ctctgaaatc acacttt                                    27

<210> SEQ ID NO 15
<211> LENGTH: 24
<212> TYPE: DNA
<213> ORGANISM: Artificial Sequence
<220> FEATURE:
<223> OTHER INFORMATION: PCR Primer

<400> SEQUENCE: 15
ctgacatcta tatctgcaac ctgg                                       24

<210> SEQ ID NO 16
<211> LENGTH: 24
<212> TYPE: DNA
<213> ORGANISM: Artificial Sequence
<220> FEATURE:
<223> OTHER INFORMATION: PCR Primer

<400> SEQUENCE: 16
tgcagagagg cccccaaac accc                                        24

<210> SEQ ID NO 17
<211> LENGTH: 19
<212> TYPE: DNA
<213> ORGANISM: Artificial Sequence
<220> FEATURE:
<223> OTHER INFORMATION: PCR Primer

<400> SEQUENCE: 17
tgtggctgat ttggtccac                                             19

<210> SEQ ID NO 18
<211> LENGTH: 23
<212> TYPE: DNA
<213> ORGANISM: Artificial Sequence
<220> FEATURE:
<223> OTHER INFORMATION: PCR Primer

<400> SEQUENCE: 18
cctcgggccc attggtgaat aag                                        23

<210> SEQ ID NO 19
<211> LENGTH: 25
<212> TYPE: DNA
<213> ORGANISM: Artificial Sequence
<220> FEATURE:
<223> OTHER INFORMATION: PCR Primer

<400> SEQUENCE: 19
ttgtgtggaa ttgtgagcgg ataac                                      25

<210> SEQ ID NO 20
<211> LENGTH: 25
<212> TYPE: DNA
<213> ORGANISM: Artificial Sequence
<220> FEATURE:
<223> OTHER INFORMATION: PCR Primer

<400> SEQUENCE: 20
cccaggcttt acactttatg cttcc                                      25

<210> SEQ ID NO 21
<211> LENGTH: 20
<212> TYPE: DNA
<213> ORGANISM: Artificial Sequence
```

-continued

```
<220> FEATURE:
<223> OTHER INFORMATION: PCR Primer

<400> SEQUENCE: 21
ggggatgtgc tgcaaggcga                                              20

<210> SEQ ID NO 22
<211> LENGTH: 22
<212> TYPE: DNA
<213> ORGANISM: Artificial Sequence
<220> FEATURE:
<223> OTHER INFORMATION: PCR Primer

<400> SEQUENCE: 22
ccagggtttt cccagtcacg ac                                           22
```